United States Patent
Bolle et al.

(10) Patent No.: US 8,263,508 B2
(45) Date of Patent: Sep. 11, 2012

(54) PHOSPHOSILICATE GLASS CERAMIC

(75) Inventors: Urs Bolle, Koblach (AT); Marcel Schweiger, Chur (CH); Elke Apel, Sevelen (CH); Wolfram Höland, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 206 days.

(21) Appl. No.: 12/630,024

(22) Filed: Dec. 3, 2009

(65) Prior Publication Data

US 2011/0021336 A1     Jan. 27, 2011

(30) Foreign Application Priority Data

Jul. 24, 2009   (EP) .................... 09009626

(51) Int. Cl.
*C03C 10/16* (2006.01)
*C03C 10/04* (2006.01)
*C03C 10/10* (2006.01)
*C09K 3/00* (2006.01)

(52) U.S. Cl. ........ 501/3; 501/5; 501/6; 106/35; 65/33.3; 65/33.7

(58) Field of Classification Search ............ 501/2, 3, 501/5, 6, 10; 106/35; 65/33.1, 33.3, 33.7
See application file for complete search history.

(56) References Cited

U.S. PATENT DOCUMENTS

| | | | |
|---|---|---|---|
| 5,698,019 A | 12/1997 | Frank et al. | |
| 7,166,548 B2 * | 1/2007 | Apel et al. | 501/5 |
| 7,183,232 B2 * | 2/2007 | van't Hoen et al. | 501/10 |
| 7,371,702 B2 * | 5/2008 | Ritzberger et al. | 501/10 |
| 2006/0205582 A1 * | 9/2006 | van't Hoen et al. | 501/8 |

FOREIGN PATENT DOCUMENTS

| | | |
|---|---|---|
| DE | 4423793 C1 | 2/1996 |
| DE | 19725555 A1 | 12/1998 |
| DE | 10351885 A1 | 5/2004 |
| DE | 102004013455 B3 | 9/2005 |

* cited by examiner

*Primary Examiner* — Noah Wiese
(74) *Attorney, Agent, or Firm* — Ann M. Knab; Thad McMurray

(57) ABSTRACT

A phosphosilicate glass ceramic with nanoscale fluoroapatite and leucite crystals. The glass ceramic is very similar to natural tooth material in terms of its optical properties. The glass ceramic has a low linear thermal expansion coefficient and a low pressing temperature and is therefore particularly suitable for pressing on metal alloys to produce dental restoration.

42 Claims, No Drawings

PHOSPHOSILICATE GLASS CERAMIC

CROSS-REFERENCE TO RELATED APPLICATIONS

The present application claims priority to European Patent Application Serial No. 09009626.4 filed Jul. 24, 2009, the entirety of which is hereby incorporated by reference.

BACKGROUND OF THE INVENTION

1. Field of the Invention

The present invention relates to phosphosilicate glass ceramic, and, more specifically, to a phosphosilicate glass ceramic which comprises fluoroapatite crystals and leucite crystals, is chemically stable, is esthetically very attractive, and is suitable for the preparation of dental restorations and in particular for pressing on dental alloys.

2. Description of the Related Art

Phosphosilicate glass ceramics are known in the prior art. In some cases, they contain fluoroapatite and/or leucite as main or secondary crystal phase.

German Patent No. 4423793 describes a phosphosilicate glass ceramic which, in addition to a leucite main crystal phase, comprises at least one further crystal phase and one or more glass phases. The secondary crystal phase can comprise rod- or needle-shaped apatite crystals, such as fluoroapatite, which have a length greater than 2 μm. However, a high CaO content is necessary to precipitate needle-like fluoroapatite crystals. Furthermore, the high leucite content of the glass ceramic necessitates relatively high processing temperatures of up to 1200° C. to mould the glass ceramic by pressing into the desired dental framework, i.e. to achieve a viscous flow of the glass ceramic. Moreover, the high leucite content results in a high linear expansion coefficient in the range of about $15 \times 10^{-6} K^{-1}$ to about $20 \times 10^{-6} K^{-1}$. The glass ceramic is therefore not suitable for the coating of materials with low expansion coefficients such as specific metal alloys.

German Patent No. 19725555 describes a translucent glass ceramic, the main crystal phase of which consists of fluoroapatite crystals. In addition, depending on the composition of the starting glass used, further crystal phases can be formed, but not a leucite phase. The glass ceramic has a thermal expansion coefficient of $6.0 \times 10^{-6} K^{-1}$ to $12.0 \times 10^{-6} K^{-1}$. This limits the use of the glass ceramic, as it can be employed only to coat or veneer dental framework made of materials with a very low expansion coefficient, such as lithium disilicate glass ceramics or titanium. In addition, very high processing temperatures of up to 1200° C. are also necessary to mould the glass ceramic by pressing into the desired dental structure.

BRIEF SUMMARY OF THE INVENTION

It is therefore a principal object and advantage of the present invention to provide a phosphosilicate glass ceramic which is very similar to natural tooth material in terms of optical properties.

It is another object and advantage of the present invention to provide a phosphosilicate glass ceramic with apatite crystals that are in the nanoscale range.

It is yet another object and advantage of the present invention to provide a phosphosilicate glass ceramic that has a low linear thermal expansion coefficient and a low pressing temperature.

It is a further object and advantage of the present invention to provide a phosphosilicate glass ceramic that is particularly suitable for pressing on metal alloys.

Other objects and advantages of the present invention will in part be obvious, and in part appear hereinafter.

In accordance with the foregoing objects and advantages, the present invention provides a phosphosilicate glass ceramic which, despite a very small CaO content, has apatite crystals which are in addition very small and in particular in the nanoscale range, and which is thereby very similar to the natural tooth material in terms of its optical properties. Furthermore, the glass ceramic should have a low linear thermal expansion coefficient and a low pressing temperature and is therefore particularly suitable for pressing on metal alloys.

DETAILED DESCRIPTION OF THE INVENTION

The phosphosilicate glass ceramic according to the invention is characterized in that it comprises the following components:

$SiO_2$ 57.6-62.0 wt.-%
$Al_2O_3$ 12.0-16.0 wt.-%
$B_2O_3$ 0.0-1.5 wt.-%
$K_2O$ 9.0-13.0 wt.-%
$Na_2O$ 5.0-8.0 wt.-%
$Li_2O$ 0.0-1.5 wt.-%
$BaO$ 0.0-2.5 wt.-%
$CaO$ 0.6-2.4 wt.-%
$ZnO$ 0.0-3.0 wt.-%
$TiO_2$ 0.0-1.5 wt.-%
$ZrO_2$ 0.0-3.5 wt.-%
$CeO_2$ 0.0-1.0 wt.-%
$P_2O_5$ 0.4-2.5 wt.-%
$F$ 0.3-1.5 wt.-% and further comprises fluoroapatite crystals and leucite crystals.

The glass ceramic according to the invention is characterized in that it surprisingly contains fluoroapatite crystals in the glass phase, despite having very small quantities of CaO compared with conventional glass ceramics. In conventional glass ceramics, on the other hand, a CaO quantity of at least 2.5 wt.-% is necessary to bring about the formation of rod- or needle-like phosphate-containing crystals.

Furthermore, the glass ceramic according to the invention has very small quantities of fluoroapatite and leucite crystals compared with known glass ceramics, which leads to a markedly advantageous combination of properties. In addition to excellent optical properties, the glass ceramic according to the invention has a heat expansion coefficient which makes it suitable for a large number of ways of processing, and it has a low pressing temperature.

In a preferred embodiment, the phosphosilicate glass ceramic according to the invention is characterized in that it comprises the following components independently of each other in amounts of:

$SiO_2$ 58.0-61.5 wt.-%, preferably 58.0-61.0 wt.-%
$Al_2O_3$ 12.0-15.0 wt.-%, preferably 13.0-14.5 wt.-%
$B_2O_3$ 0.1-1.2 wt.-%, preferably 0.1-0.8 wt.-%
$K_2O$ 9.0-12.5 wt.-%, preferably 9.0-12.0 wt.-%
$Na_2O$ 5.5-8.0 wt.-%, preferably 6.0-8.0 wt.-%
$Li_2O$ 0.0-1.0 wt.-%, preferably 0.1-0.8 wt.-%
$BaO$ 0.0-2.0 wt.-%, preferably 0.0-1.5 wt.-%
$CaO$ 1.0-2.4 wt.-%, preferably 1.2-2.2 wt.-%
$ZnO$ 0.0-2.7 wt.-%, preferably 0.1-2.5 wt.-%
$TiO_2$ 0.2-1.5 wt.-%, preferably 0.2-1.3 wt.-%
$ZrO_2$ 0.8-3.5 wt.-%, preferably 0.8-3.0 wt.-%
$CeO_2$ 0.2-1.0 wt.-%, preferably 0.3-0.9 wt.-%
$P_2O_5$ 0.4-2.2 wt.-%, preferably 0.4-2.0 wt.-%
$F$ 0.5-1.5 wt.-%, preferably 0.6-1.5 wt.-%.

By "independently of each other" is meant that at least one of the components is present in the given preferred amount. For example, it is possible that only the $SiO_2$ is present in an amount corresponding to the preferred embodiment of 58.0 to 61.5 wt.-%.

Moreover, it is preferred that the glass ceramic has needle-shaped fluoroapatite crystals and preferably very small fluoroapatite crystals. Those crystals are preferred which have a maximum extension of less than 500 nm, preferably less than 250 nm, and particularly preferably less than 100 nm. In order to determine the maximum extension of the crystals, their length in the c-axis direction was measured using scanning electron photographs. Particularly preferably, the fluoroapatite crystals have a length of less than 100 nm and a width of no more than 60 nm. It was surprisingly found that the fluoroapatite crystals in the glass ceramic according to the invention are not subject to Ostwald ripening which would otherwise lead to the formation of larger crystals at the expense of the number of smaller crystals. In particular, the small fluoroapatite crystals result in the desired optical properties of the glass ceramic, i.e. they lead to a marked optical similarity to the natural tooth material.

Furthermore, the translucency of the glass ceramic according to the invention is surprisingly not substantially impaired by the leucite crystals contained therein. This is presumably caused by the fact that the special composition according to the invention leads to only a small degree of leucite crystallization.

The glass ceramic according to the invention preferably has a linear thermal expansion coefficient of 11.0 to $15.0 \times 10^{-6} K^{-1}$, and in particular 11.5 to $14.0 \times 10^{-6} K^{-1}$, measured in a temperature range of 100 to 400° C.

It is moreover particularly advantageous that the glass ceramic according to the invention has a low pressing temperature of usually under 1000° C., in particular 850° C. to 950° C. It can therefore be pressed on dental alloys without occurrence of a substantial deformation of the alloys. Such a deformation is very disadvantageous in the preparation of accurately-fitting restorations.

The expansion coefficient and the pressing temperature are important properties in connection with the preferred use of the glass ceramic according to the invention for the preparation of dental restorations. The glass ceramic according to the invention is suitable in particular as a coating material for metal alloys which serve as framework materials. The expansion coefficient of the glass ceramic should usually be about 10% less than the expansion coefficient of the framework material to obtain a stable dental restoration. Thereby the high stresses which could lead to chips or cracks are avoided.

The invention further relates to a process for the preparation of the phosphosilicate glass ceramic according to the invention, wherein: (a) a glass comprising the components according to the invention is melted at temperatures of 1500 to 1550° C.; (b) the glass melt obtained is poured into water to form a glass granulate; (c) optionally, the glass granulate is comminuted to a glass powder with an average particle size of less than 90 μm, preferably 10 to 40 μm; and (d) the glass granulate or the glass powder are subjected to a heat treatment in a temperature range of 500° C. to 1000° C. for a period of 30 minutes to 6 hours to form the glass ceramic.

In step (a) of the process, a starting glass is first melted by intimately mixing suitable materials, such as for example carbonates, oxides and fluorides, with one another and heating them to the given temperatures. Then, in step (b), the glass melt obtained is quenched by pouring it into water and thereby transformed into a glass granulate. This procedure is usually also called fitting. Optionally, the glass granulate is then comminuted in step (c) and in particular ground to the desired particle size with customary mills.

In step (d), the glass granulate or optionally the glass powder are subjected to a thermal treatment at a temperature in the range of 500° C. to 1000° C., preferably at about 950° C., for a period of 30 minutes to 6 hours, preferably about 1 hour, whereupon the glass ceramic forms.

Finally, the invention also relates to the use of the glass ceramic according to the invention as: (a) a dental material or a dental product shaped therefrom; or (b) a constituent of dental materials or dental products shaped therefrom. In addition to blanks shaped as desired, dental restorations such as an inlay, an onlay, a bridge, an abutment, a veneer, a shell, a facing, a facet, a filling, a connector, a crown or a partial crown, are shaped dental products. The blanks usually have shapes such as are used in conventional pressing devices, such as press furnaces, e.g. small discs, blocks or cylinders.

In a preferred embodiment, the phosphosilicate glass ceramic according to the present invention is pressed onto a dental framework to produce a shaped dental product, wherein the dental framework is preferably based on a dental alloy. The pressing on preferably takes place at a temperature of less than 1000° C. and in particular at 850-950° C.

Particularly advantageous are those dental alloys which have a linear thermal expansion coefficient exceeding that of the glass ceramic according to the invention by about 10%. The phosphosilicate glass ceramic according to the invention is in particular suitable for pressing onto a dental alloy which has a linear thermal expansion coefficient of 13.5 to $15.5 \times 10^{-6} K^{-1}$, measured in a temperature range of 100 to 400° C.

The invention therefore also relates to a process for the preparation of a dental product, in particular a dental restoration, wherein: (a) a dental framework, in particular based on a dental alloy, is provided, and (b) the dental framework is coated with the glass ceramic according to the invention, in particular by pressing the glass ceramic on the dental framework.

The invention is explained in more detail below by means of examples.

EXAMPLES 1-9

Examples 1 through 9 examine the composition, preparation, and properties of glass ceramics according to the present invention. In these Examples, a total of 9 different glass ceramics were prepared according to the invention with the compositions described in Table 1, where "FAP"=fluoroapatite and amounts are in weight percent.

TABLE 1

| Examples | 1 | 2 | 3 | 4 | 5 | 6 | 7 | 8 | 9 |
|---|---|---|---|---|---|---|---|---|---|
| $SiO_2$ | 58.60 | 57.60 | 60.00 | 58.89 | 61.00 | 57.60 | 59.90 | 62.00 | 57.60 |
| $K_2O$ | 10.51 | 11.95 | 9.51 | 9.51 | 12.50 | 10.60 | 9.00 | 13.00 | 10.00 |
| $Na_2O$ | 6.35 | 6.20 | 6.35 | 6.35 | 5.50 | 8.00 | 7.50 | 5.00 | 8.00 |
| $Al_2O_3$ | 13.87 | 13.95 | 13.75 | 14.30 | 14.50 | 12.90 | 13.50 | 12.00 | 13.00 |
| BaO | 1.83 | 1.82 | 1.82 | 1.85 | 1.00 | 2.00 | — | 0.50 | 2.10 |

TABLE 1-continued

| Examples | 1 | 2 | 3 | 4 | 5 | 6 | 7 | 8 | 9 |
|---|---|---|---|---|---|---|---|---|---|
| CaO | 1.87 | 1.87 | 1.87 | 1.87 | 2.40 | 2.20 | 1.50 | 0.60 | 2.30 |
| $P_2O_5$ | 0.46 | 0.46 | 0.46 | 0.60 | 0.80 | 0.70 | 0.40 | 2.50 | 0.70 |
| $B_2O_3$ | 0.10 | 0.10 | 0.10 | 0.10 | — | 0.50 | 0.20 | 0.40 | 0.50 |
| $TiO_2$ | 0.61 | 0.59 | 0.63 | 0.63 | — | — | 1.50 | 0.80 | — |
| $ZrO_2$ | 1.36 | 1.20 | 1.30 | 1.40 | 0.80 | 1.00 | 3.50 | 1.00 | 1.00 |
| ZnO | 2.58 | 2.40 | 2.35 | 2.64 | — | 3.00 | 1.50 | — | 3.00 |
| $CeO_2$ | 0.76 | 0.76 | 0.76 | 0.76 | 1.00 | — | 0.60 | 0.90 | 0.30 |
| F | 1.10 | 1.10 | 1.10 | 1.10 | 0.50 | 1.50 | 0.90 | 1.30 | 1.50 |
| Phases | FAP*/leucite | FAP*/leucite | FAP*/leucite | FAP*/leucite | FAP*/leucite | FAP*/leucite | FAP*/leucite | FAP*/leucite | FAP*/leucite |

To prepare the glass ceramics, the respective composition was melted from suitable oxides, carbonates, and fluorides in a platinum-rhodium crucible at a temperature of about 1500° C. to 1550° C. and for a homogenization time of 1 hour. The glass melt was quenched in water and the formed granulate of the starting glass was dried and ground to an average particle size of less than 90 μm. The granulate or the obtained powder of the starting glass were then subjected for between 30 minutes to 6 hours to a single- or multi-stage heat treatment at more than 500° C. and up to 1000° C., whereupon the glass ceramic formed.

Table 2 details selected properties for some of the glass ceramics that were determined from the respective testpieces. Table 2 also gives details of the specifically chosen heat treatment of the starting glass under "Thermal treatment". The examples illustrate how glass ceramics with different properties can be obtained by altering the chemical composition.

TABLE 2

| Examples | 2 | 4 | 6 | 9 |
|---|---|---|---|---|
| Thermal treatment [° C./hr] | 950/1 | 950/1 | 950/1 | 950/1 |
| Preparation of blanks by sintering at [° C./hr] | | 880/0.5 | | 810/0.5 |
| α-value of sintered glass ceramic [×$10^{-6}K^{-1}$] 100-400° C. (see process A described below) | 15.0 | 9.6 | 13.2 | 12.0 |
| Tg of sintered glass ceramic [° C.] | 472 | 566 | 478 | 490 |
| Pressing temperature [° C.] | | 950 | | 880 |
| α-value of sintered blank after pressing [×$10^{-6}K^{-1}$] 100-400° C. (see process B described below) | | 11.8 | | 13.1 |
| Tg of pressed ceramic [° C.] | | 547 | | 477 |
| Biaxial strength [MPa] | | 102 ± 18 | | |
| Acetic acid solubility [μg/cm$^2$] | | 12 | | |
| Saliva solubility [μg/cm$^2$] | | 20 | | |

The linear thermal expansion coefficient α ("α-value") in Table 2 was measured using one of two processes. For the first process ("process A"), a rod-like green compact was prepared from the powder of the respective glass ceramic and sintered in a vacuum furnace at a heating rate of 60° C./min and with a holding time of 1 minute at the respective firing temperature. A glazing firing without vacuum was then carried out at a final temperature higher by 20° C. and with a holding time of 1 minute. Monolithic sintered blanks were also prepared via the sintering process in the second process ("process B"). For process B, the starting powder was compressed into a green compact by means of a uniaxial press at 500 to 1000 bar pressure and then fully sintered under vacuum. The sintered blanks were pressed into the test geometry in a hot press furnace at 850 to 950° C. and at a compression pressure of 19 to 22 bar.

The linear thermal expansion coefficient α was then determined in case of examples 2, 4, 6 and 9 on sintered glass ceramic testpieces according to process A and in case of examples 4 and 9 also on hot-pressed glass ceramic testpieces according to process B in a temperature range of 100 to 400° C.

The acid and saliva resistance values in Table 2 were measured using the following methods. Acid resistance is a measure of the chemical resistance specifically of glasses and glass ceramics used in dentistry since these are permanently exposed to the effect of acid substances in the oral cavity. The acid resistance was determined according to ISO specification 6872:1995. For this, small test discs with a diameter of 12 mm and a thickness of 1 mm were first prepared by sintering together glass ceramic powder with an average particle size of less than 90 μm. The powder was kept at the sintering temperature for 1 minute. The small test discs were then treated for 16 hours in a Soxhlet extractor with 4 vol.-% aqueous acetic acid at 80° C. In the saliva test, the testpieces were stored for 7 days at 60° C. in artificial saliva. Finally, the loss of mass occurring was determined as a measure of the acid resistance.

The biaxial strength values in Table 2 were determined according to ISO 6872. For this, small test discs with a diameter of 13 mm and a thickness of 1.2 mm were prepared by sintering together glass ceramic powder with an average particle size of less than 90 μm. The powder was kept at the sintering temperature for 1 minute. The small discs were surface-ground and measured in a biaxial tester according to specification ISO 6872.

EXAMPLE 10

Example 10 describes the preparation of a layered ceramic by pressing the glass ceramic of the present invention onto an opacified alloy framework. In this example, the preparation of a glass ceramic according to the invention having the composition according to example 9 is described, which glass ceramic can advantageously be pressed onto an opaque alloy framework. For this, the dental alloy was first coated with a glass ceramic opaquer to cover the metallic dark colour. A starting glass was then prepared with the chemical composition given in example 9 of Table 1. For the preparation, a corresponding mixture of suitable oxides, carbonates and fluorides was melted in a platinum-rhodium crucible at a temperature of 1500° C. for a homogenization time of 1 hr. The glass melt was quenched in water and the formed granulate of the starting glass was dried and ground to an average particle size of less than 90 μm, preferably to an average particle size of 10 to 30 μm. The obtained glass powder was then subjected to a temperature treatment at 950° C. for 1 hour. The glass ceramic was subsequently ground to an average particle size of less than 90 μm, preferably to an average particle size of 20 to 40 μm.

This powder was sintered to form a rod-like green blank in a vacuum furnace at a heating rate of 60° C./min and with a holding time of 1 minute at 900° C. A thermal expansion coefficient of $12.0\times10^{-6}K^{-1}$, measured in the temperature range of 100° C. to 400° C., was determined for the sample obtained in this way.

The glass ceramic powder was fired for a 15 min holding time at 810° C. and in a vacuum into sintered blanks. These blanks were then pressed into rod-like testpieces by a hot-pressing process at 880° C. An expansion coefficient of $13.1\times10^{-6}K^{-1}$, measured in the temperature range of 100° C. to 400° C., was determined for the glass ceramic sample obtained in this way.

This glass ceramic is therefore particularly well suited to pressing onto opacified dental alloys. Two dental alloys were tested for this purpose, d.SIGN 30 (Ivoclar Vivadent AG) with an expansion coefficient of $14.5\times10^{-6}K^{-1}$ and W1 (Ivoclar Vivadent AG) with an expansion coefficient of $15.2\times10^{-6}K^{-1}$. Molar frameworks were prepared from both alloys in accordance with the specifications of the alloy manufacturer. The frameworks were made opaque with IPS InLine PoM opaquer (Ivoclar Vivadent AG) according to the manufacturer's instructions. The metal frames were then waxed up in order to have the anatomical shape of the tooth. The metal frameworks prepared in this way were embedded with Press Vest Speed embedding compound and the wax was burned out. The sintered blanks of the glass ceramic were pressed into the die at 900° C. and a pressure of 19 to 22 bar. A strong bond between opacified dental alloy and glass ceramic was achieved via the hot-pressing process in view of the adapted expansion coefficient and the adapted processing temperature. After the cooling and disembedding by sandblasting, the molar crowns were completely pressed out and free of cracks. In order to complete the dental operation, the crowns were each twice subjected to a glaze firing with IPS InLine PoM glaze (Ivoclar Vivadent AG) at 770° C. The crowns were also free of cracks after this additional thermal cycle.

EXAMPLE 11

Example 11 examines the physical structure of the glass ceramic. In order to show the structure of the glass ceramic using scanning electron microscopy, a glass ceramic with the composition according to Example 3 was first produced after thermal treatment for 1 hour at 950° C. A scanning electron microscope photograph was produced after sample preparation by etching with 3% aqueous HF solution for a period of 10 seconds. Through this etching procedure, the $SiO_2$-rich glass matrix was dissolved in a thin layer, with the result that in particular the fluoroapatite crystals emerged from the sample plane and thus became clearly visible. These crystals were isolated from each other and had a length of about 100 nm.

Although the present invention has been described in connection with a preferred embodiment, it should be understood that modifications, alterations, and additions can be made to the invention without departing from the scope of the invention as defined by the claims.

What is claimed is:

1. A phosphosilicate glass ceramic comprising:
   a plurality of fluoroapatite crystals, wherein said fluoroapatite crystals have a maximum extension of less than 100 nm;
   a plurality of leucite crystals; and
   the following components in weight percent:
   $SiO_2$ 57.6-62.0%
   $Al_2O_3$ 12.0-16.0%
   $B_2O_3$ 0.0-1.5%
   $K_2O$ 9.0-13.0%
   $Na_2O$ 5.0-8.0%
   $Li_2O$ 0.0-1.5%
   BaO 0.0-2.5%
   CaO 0.6-2.4%
   ZnO 0.0-3.0%
   $TiO_2$ 0.0-1.5%
   $ZrO_2$ 0.0-3.5%
   $CeO_2$ 0.0-1.0%
   $P_2O_5$ 0.4-2.5%
   F 0.3-1.5%.

2. The phosphosilicate glass ceramic of claim 1, wherein at least one of said components comprise the following weight percent:
   $SiO_2$ 58.0-61.5%
   $Al_2O_3$ 12.0-15.0%
   $B_2O_3$ 0.1-1.2%
   $K_2O$ 9.0-12.5%
   $Na_2O$ 5.5-8.0%
   $Li_2O$ 0.0-1.0%
   BaO 0.0-2.0%
   CaO 1.0-2.4%
   ZnO 0.0-2.7%
   $TiO_2$ 0.2-1.5%
   $ZrO_2$ 0.8-3.5%
   $CeO_2$ 0.2-1.0%
   $P_2O_5$ 0.4-2.2%
   F 0.5-1.5%.

3. The phosphosilicate glass ceramic of claim 1, wherein at least one of said components comprise the following weight percent:
   $SiO_2$ 58.0-61.0%
   $Al_2O_3$ 13.0-14.5%
   $B_2O_3$ 0.1-0.8%
   $K_2O$ 9.0-12.0%
   $Na_2O$ 6.0-8.0%
   $Li_2O$ 0.1-0.8%
   BaO 0.0-1.5%
   CaO 1.2-2.2%
   ZnO 0.1-2.5%
   $TiO_2$ 0.2-1.3%
   $ZrO_2$ 0.8-3.0%
   $CeO_2$ 0.3-0.9%
   $P_2O_5$ 0.4-2.0%
   F 0.6-1.5%.

4. The phosphosilicate glass ceramic of claim 1, wherein said fluoroapatite crystals are needle-shaped.

5. The phosphosilicate glass ceramic of claim 1, wherein said glass ceramic has a linear thermal expansion coefficient of $11.0\times10^{-6}K^{-1}$ to $15.0\times10^{-6}K^{-1}$ measured in a temperature range of 100 to 400° C.

6. The phosphosilicate glass ceramic of claim 1, wherein said glass ceramic has a linear thermal expansion coefficient of $11.5\times10^{-6}K^{-1}$ to $14.0\times10^{-6}K^{-1}$ measured in a temperature range of 100 to 400° C.

7. The phosphosilicate glass ceramic of claim 1, wherein said glass ceramic has a pressing temperature of less than 1000° C.

8. The phosphosilicate glass ceramic of claim 1, wherein said glass ceramic has a pressing temperature between 850° C. and 950° C.

9. A method for preparation of a phosphosilicate glass ceramic comprising:

a plurality of fluoroapatite crystals, wherein said fluoroapatite crystals have a maximum extension of less than 100 nm;
a plurality of leucite crystals; and
the following components in weight percent:
$SiO_2$ 57.6-62.0%
$Al_2O_3$ 12.0-16.0%
$B_2O_3$ 0.0-1.5%
$K_2O$ 9.0-13.0%
$Na_2O$ 5.0-8.0%
$Li_2O$ 0.0-1.5%
$BaO$ 0.0-2.5%
$CaO$ 0.6-2.4%
$ZnO$ 0.0-3.0%
$TiO_2$ 0.0-1.5%
$ZrO_2$ 0.0-3.5%
$CeO_2$ 0.0-1.0%
$P_2O_5$ 0.4-2.5%
F 0.3-1.5%, the method comprising:
melting a glass comprising said components at temperatures of 1500 to 1550° C.;
pouring the glass melt obtained into water to form a glass granulate;
optionally comminuting the glass granulate to a glass powder with an average particle size of less than 90 μm, preferably 10 to 40 μm; and
subjecting the glass granulate or the glass powder to a heat treatment in a temperature range of 500° C. to 1000° C. for a period of 30 minutes to 6 hours to form the glass ceramic.

10. The method of claim 9, wherein the heat treatment is carried out at a temperature of about 950° C. for a period of about 1 hour.

11. A dental material shaped from phosphosilicate glass ceramic, said phosphosilicate glass ceramic comprising:
a plurality of fluoroapatite crystals, wherein said fluoroapatite crystals have a maximum extension of less than 100 nm;
a plurality of leucite crystals; and
the following components in weight percent:
$SiO_2$ 57.6-62.0%
$Al_2O_3$ 12.0-16.0%
$B_2O_3$ 0.0-1.5%
$K_2O$ 9.0-13.0%
$Na_2O$ 5.0-8.0%
$Li_2O$ 0.0-1.5%
$BaO$ 0.0-2.5%
$CaO$ 0.6-2.4%
$ZnO$ 0.0-3.0%
$TiO_2$ 0.0-1.5%
$ZrO_2$ 0.0-3.5%
$CeO_2$ 0.0-1.0%
$P_2O_5$ 0.4-2.5%
F 0.3-1.5%.

12. The dental material of claim 11, wherein said glass ceramic comprises a constituent of said dental material.

13. The dental material of claim 11, wherein the glass ceramic is pressed onto a dental framework.

14. The dental material of claim 13, wherein the pressing on takes place at a temperature of less than 1000° C.

15. The dental material of claim 13, wherein the pressing on takes place at a temperature between 850 to 950° C.

16. The dental material of claim 13, wherein the dental framework is based on a dental alloy.

17. The dental material of claim 16, wherein the dental alloy has a linear expansion coefficient between $13.5 \times 10^{-6} K^{-1}$ and $15.5 \times 10^{-6} K^{-1}$ measured in a temperature range of 100 to 400° C.

18. A dental product shaped from phosphosilicate glass ceramic, said phosphosilicate glass ceramic comprising:
a plurality of fluoroapatite crystals, wherein said fluoroapatite crystals have a maximum extension of less than 100 nm;
a plurality of leucite crystals; and
the following components in weight percent:
$SiO_2$ 57.6-62.0%
$Al_2O_3$ 12.0-16.0%
$B_2O_3$ 0.0-1.5%
$K_2O$ 9.0-13.0%
$Na_2O$ 0.5-8.0%
$Li_2O$ 0.0-1.5%
$BaO$ 0.0-2.5%
$CaO$ 0.6-2.4%
$ZnO$ 0.0-3.0%
$TiO_2$ 0.0-1.5%
$ZrO_2$ 0.0-3.5%
$CeO_2$ 0.0-1.0%
$P_2O_5$ 0.4-2.5%
F 0.3-1.5%.

19. The dental product of claim 18, wherein said glass ceramic comprises a constituent of said dental product.

20. The dental product of claim 8, wherein the glass ceramic is pressed onto a dental framework.

21. The dental product of claim 20, wherein the pressing on takes place at a temperature of less than 1000° C.

22. The dental product of claim 20, wherein the pressing on takes place at a temperature between 850 to 950° C.

23. The dental product of claim 20, wherein the dental framework is based on a dental alloy.

24. The dental product of claim 23, wherein the dental alloy has a linear expansion coefficient between $13.5 \times 10^{-6} K^{-1}$ and $15.5 \times 10^{-6} K^{-1}$ measured in a temperature range of 100 to 400° C.

25. A phosphosilicate glass ceramic consisting essentially of:
a plurality of fluoroapatite crystals;
a plurality of leucite crystals; and
the following components in weight percent:
$SiO_2$ 57.6-62.0%
$Al_2O_3$ 12.0-16.0%
$B_2O_3$ 0.0-1.5%
$K_2O$ 9.0-13.0%
$Na_2O$ 5.0-8.0%
$Li_2O$ 0.0-1.5%
$BaO$ 0.0-2.5%
$CaO$ 0.6-2.4%
$ZnO$ 0.0-3.0%
$TiO_2$ 0.0-1.5%
$ZrO_2$ 0.0-3.5%
$CeO_2$ 0.0-1.0%
$P_2O_5$ 0.4-2.5%
F 0.3-1.5%.

26. The phosphosilicate glass ceramic of claim 25, wherein said fluoroapatite crystals are needle-shaped.

27. The phosphosilicate glass ceramic of claim 25, wherein said fluoroapatite crystals have a maximum extension of less than 500 nm.

28. The phosphosilicate glass ceramic of claim 25, wherein said fluoroapatite crystals have a maximum extension of less than 250 nm.

29. The phosphosilicate glass ceramic of claim 25, wherein said fluoroapatite crystals have a maximum extension of less than 100 nm.

30. The phosphosilicate glass ceramic of claim 25, wherein said glass ceramic has a linear thermal expansion coefficient of $11.0 \times 10^{-6} K^{-1}$ to $15.0 \times 10^{-6} K^{-1}$ measured in a temperature range of 100 to 400° C.

31. The phosphosilicate glass ceramic of claim 25, wherein said glass ceramic has a linear thermal expansion coefficient of $11.5 \times 10^{-6} K^{-1}$ to $14.0 \times 10^{-6} K^{-1}$ measured in a temperature range of 100 to 400° C.

32. The phosphosilicate glass ceramic of claim 25, wherein said glass ceramic has a pressing temperature of less than 1000° C.

33. The phosphosilicate glass ceramic of claim 25, wherein said glass ceramic has a pressing temperature between 850° C. and 950° C.

34. A phosphosilicate glass ceramic comprising:
a plurality of fluoroapatite crystals;
a plurality of leucite crystals; and
the following components in weight percent:
$SiO_2$ 57.6-62.0%
$Al_2O_3$ 12.0-16.0%
$B_2O_3$ 0.0-1.5%,
$K_2O$ 9.0-13.0%
$Na_2O$ 5.0-8.0%
$Li_2O$ 0.0-1.5%
BaO 0.0-2.5%
CaO 0.6-2.4%
ZnO 0.1-3.0%
$TiO_2$ 0.0-1.5%
$ZrO_2$ 0.0-3.5%
$CeO_2$ 0.0-1.0%
$P_2O_5$ 0.4-2.5%
F 0.3-1.5%.

35. The phosphosilicate glass ceramic of claim 34, wherein said fluoroapatite crystals are needle-shaped.

36. The phosphosilicate glass ceramic of claim 34, wherein said fluoroapatite crystals have a maximum extension of less than 500 nm.

37. The phosphosilicate glass ceramic of claim 34, wherein said fluoroapatite crystals have a maximum extension of less than 250 nm.

38. The phosphosilicate glass ceramic of claim 34, wherein said fluoroapatite crystals have a maximum extension of less than 100 nm.

39. The phosphosilicate glass ceramic of claim 34, wherein said glass ceramic has a linear thermal expansion coefficient of $11.0 \times 10^{-6} K^{-1}$ to $15.0 \times 10^{-6} K^{-1}$ measured in a temperature range of 100 to 400° C.

40. The phosphosilicate glass ceramic of claim 34, wherein said glass ceramic has a linear thermal expansion coefficient of $11.5 \times 10^{-6} K^{-1}$ to $14.0 \times 10^{-6} K^{-1}$ measured in a temperature range of 100 to 400° C.

41. The phosphosilicate glass ceramic of claim 34, wherein said glass ceramic has a pressing temperature of less than 1000° C.

42. The phosphosilicate glass ceramic of claim 34, wherein said glass ceramic has a pressing temperature between 850° C. and 950° C.

* * * * *